United States Patent [19]

Nilsson et al.

[11] 4,182,316

[45] Jan. 8, 1980

[54] HOLOGRAPHIC INSTALLATION

[75] Inventors: Kenth Nilsson, Akersberga; Bertil Höek, Upsala; Thomas Ohlsson, Vällingby; Hans Bjelkhagen, Stockholm, all of Sweden

[73] Assignee: Siemens Aktiengesellschaft, Berlin & Munich, Fed. Rep. of Germany

[21] Appl. No.: 844,909

[22] Filed: Oct. 25, 1977

[30] Foreign Application Priority Data

Oct. 25, 1976 [DE] Fed. Rep. of Germany ....... 2648282

[51] Int. Cl.² .................................................. A61B 5/10
[52] U.S. Cl. ...................................... 128/665; 128/782
[58] Field of Search .............. 128/2 S, 2 R, 2 A, 2 V, 128/2.05 R, 2.05 Z, 2.06 R

[56] References Cited

U.S. PATENT DOCUMENTS

| 2,933,081 | 4/1960 | Passannante | 128/2.06 R |
| 3,605,724 | 9/1971 | Flaherty | 128/2 V |
| 3,626,932 | 12/1971 | Becker | 128/2.06 R |
| 3,871,360 | 3/1975 | Van Horn et al. | 128/2.05 R |
| 3,954,098 | 5/1976 | Dick et al. | 128/2.05 Z |

FOREIGN PATENT DOCUMENTS 2073858 10/1971 France ..................................... 128/2 A

OTHER PUBLICATIONS

Zivi et al., "Chest Motion . . . Interferometry", Med. Res. Eng., Jun. 1970, pp. 5–7.
Greguss, "Holographic Interferometry . . . ", Optics & Laser Tech., Aug. 1976, pp. 153–159.

Primary Examiner—Lee S. Cohen
Attorney, Agent, or Firm—Hill, Van Santen, Steadman, Chiara & Simpson

[57] ABSTRACT

A holographic system for recording movements of body surfaces of a patient characterized by a source of coherent light projecting on the body surface to create an object wave and having a portion of the light as a reference wave, a film carrier for photographic film disposed to simultaneously record the object and reference waves as a hologram and switching devices which are activated by a transmitter device sensing cardiac activity for double pulse switching of the source at predetermined intervals so that the two separate holograms of the body surface are recorded with each hologram being at a different time interval of the movement of the body. The present invention enables the two holograms which are recorded on the film to be recorded at given points in a cardiac activity of the patient such as given points of the EKG cycle of the patient.

2 Claims, 3 Drawing Figures

HOLOGRAPHIC INSTALLATION

BACKGROUND OF THE INVENTION

1. Field of the Invention

The present invention is directed to a holographic system for recording two separate holograms of a body surface of a patient with the holograms being spaced apart by a time interval so that movement of the body surface can be determined.

2. Prior Art

In phono cardiography, it is obvious to detect movement of the body surface, which movement is caused by the heartbeat, with the aid of microphones or a plurality of microphones. To detect this movement, it is possible to move the microphones between different points of measurement and to compare the signals which are received. However, such a method of determining body movement is based on the assumption that the signals are stationary. In addition, a number of microphones can be adjacently applied on the body surface. However, the latter will effect the movement by virtue of their weight and the spatial resolution is greatly restricted by virtue of their size.

In an article from *Medical Research Engineering*, June 1970, pages 5–7, a system for photographically determining a movement of a body surface of a patient is disclosed. In this system, a portion of light from a laser is directed on the patient's surface to produce an object wave and another portion of the laser beam is utilized as a reference wave with the reference and object waves being recorded to form a holographic recording of the body surface of the patient. To detect the image of the movement, the same film is exposed twice in succession by recording a hologram each time the laser is pulsed. Thus, two superimposed images or holograms are recorded on the film. If the subject moves between the two light flashes of the laser, a pattern will result on the film, which after development and upon illumination with coherent light such as a reference wave, will contain in addition to an image of the subject, interference fringes which enable interpretation of the movement of the body surface. The installation or system described in this article was intended for detecting respiratory movement of the human body. The laser, which functions as a light source, was turned on or actuated manually. However, a manual actuation of the laser permits only a very rough determination of the photographic time intervals and is at best applicable for the purpose for detecting a respiratory movement.

SUMMARY OF THE INVENTION

The present invention is directed to producing a holographic installation which makes it possible to detect the movement of the body surface occurring due to cardiac activity as a consequence of the pulsation of the heart and of the blood vessels. The invention provides a holographic recording with an improved spatial resolution to supplement the pulse and sound recording.

To accomplish these tasks, a holographic system for recording movement of the body surface of a patient with said system including a source of coherent light for projecting light on the body surface to create an object wave and having means for creating a reference wave, a film carrier for photographic film disposed to simultaneously record the object and reference waves to form a hologram of the body surface, and switch means for double pulse switching of said source at predetermined intervals so that two separate holograms of the body surface are recorded with each hologram being at a different time interval of the movement of the body surface, the improvement comprising a transmitter means for sensing cardiac activity of the patient and creating a signal to activate said switch means.

In accordance with the present invention, the object is achieved by virtue of the fact that the switch means are operated or actuated by a transmitter means which creates a signal that is derived from the cardiac activity of the patient. In the inventive installation, there is an automatic switching on of the light source, which may be a laser, at for example a predetermined interval of the cardiac activity which intervals are important in terms of interpretating or evaluating the movement of the body surface. These intervals can be precisely determined by using points of the EKG cycle. Due to the fact that the instantaneous image is obtained, the present invention makes is possible to bring occurrences at discrete sections of the body into correlation with one another.

DESCRIPTION OF THE PREFERRED EMBODIMENT

Figures 1, 2:
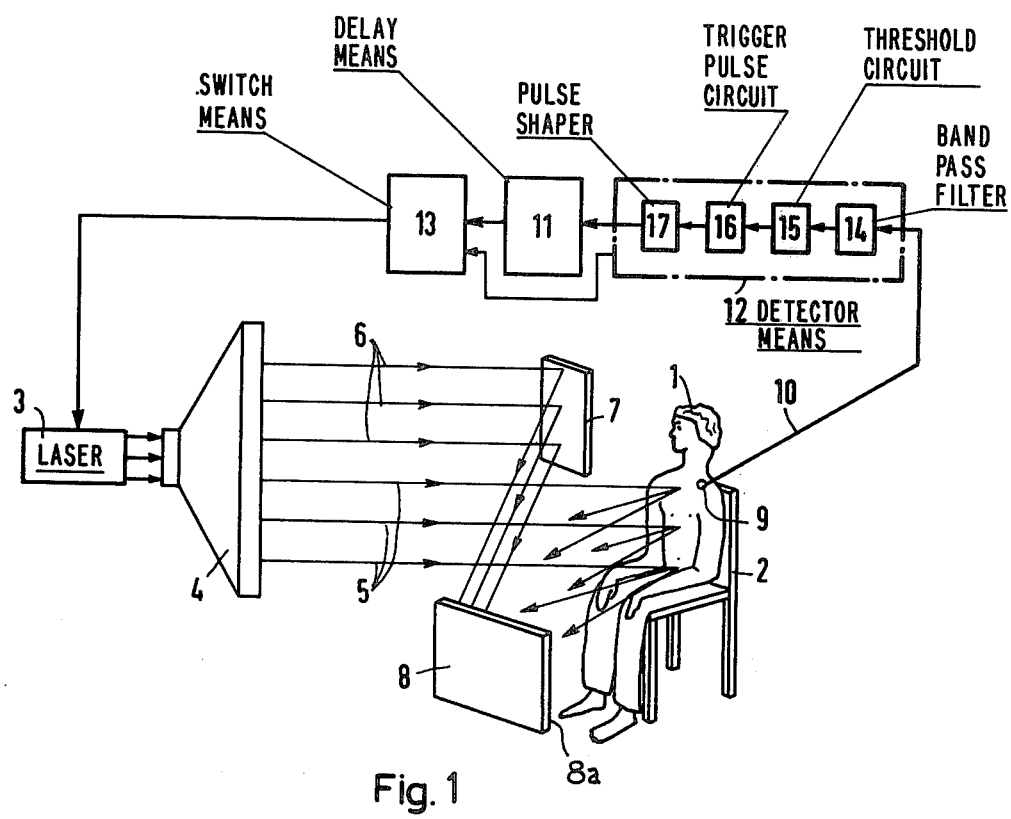
FIG. 1 illustrates a holographic system in accordance with the present invention.
FIG. 2 is a sample image of a hologram prepared by the installation of FIG. 1.

The principles of the present invention are particularly useful in a holographic system schematically illustrated in FIG. 1.

In the system of FIG. 1, a patient 1 is seated in a chair 2. In order to determine the movements of an anterior chest wall of the patient 1, which movements are brought about by cardiac activity and the pulsation of blood in the blood vessels, a laser 3 is provided, and via lenses 4 directs one portion 5 of its radiation on the chest wall of the patient to produce an object wave. Another portion 6 is guided by means for creating a reference wave illustrated as a reflector 7 on a film carrier 8 which has film 8a. As illustrated, the film carrier 8 is positioned to receive both the object wave, which is reflected from the chest surface of the patient 1, as it receives the reference wave to record a holographic recording of the chest surface.

The holographic system, which has been described hereinabove is a known system for photographing holograms. The optical density or the tone density of the film 8a produced by light radiations 5 and 6 is caused by the interference between the reference wave formed by the beam 6 and the object wave formed by the beams 5 reflected from the surface of the patient.

In order to record each of the holograms at the desired intervals of the movement, a transmitter means 9 is disposed on the patient to produce a signal which is dependent upon cardiac activity. The transmitter means 9 may be an electrode of an electrocardiogram so that the signal which is applied on line 10 represents an electrocardiogram signal or an EKG signal. The EKG signal produced by the transmitter means 9 is delivered to a signal processing means, which consists of a delay means 11 and a detector means 12. The detector means 12 effects a switching on of the laser 3 during an EKG period or cycle at a predetermined point by actuating switch means 13. In addition, the laser is switched for a second time during a EKG period after this predetermined point subsequent to the expiration of a predetermined period of time. Thus, the laser 3 is switched on twice during an EKG period or cycle so that the film 8a on the film carrier 8 is exposed twice in the course of one EKG cycle.

As illustrated, detector means 12 is a so-called QRS detector for the detection of QRS complexes of an EKG signal. The detector 12 consists of a band pass filter 14, which is adapted to the frequency spectrum of the QRS complex, a threshold circuit 15, which will deliver a pulse when the output signal of filter 14 exceeds a specific threshold value, a trigger pulse circuit 16, and a pulse shaper 17. The detector 12 is commercially available for example a Siemens module unit "heart rate meter 820" can be utilized for the detector 12.

Figure 3:
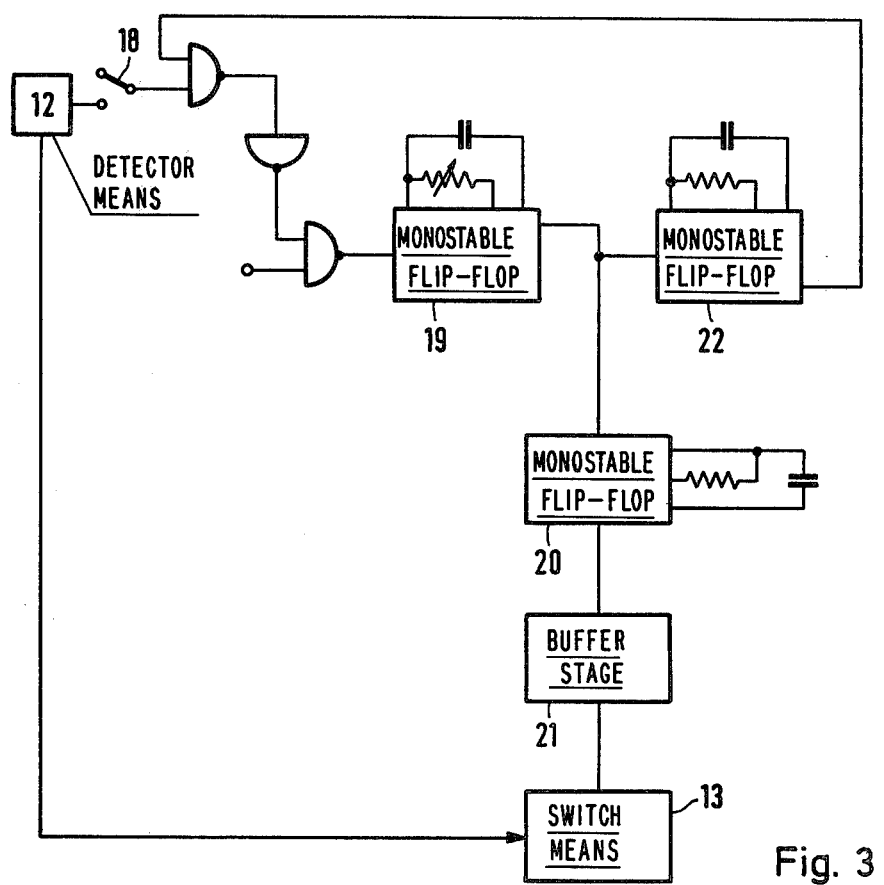
FIG. 3 illustrates a circuit detail of a delay means of the installation of FIG. 1.

The delay means 11 is best illustrated in FIG. 3. When a switch 18 is depressed, a signal from the detector 12 reaches a monostable flip-flop 19, which delivers a pulse whose duration or length is adjustable. A monostable flip-flop 20 is synchronized by the reverse or return motion of the pulse from the flip-flop 19 and delivers a new pulse with an adjustable delay. The pulse of the flip-flop 20, which has a duration of 1 ms is delivered to a buffer stage 21 and then to a switch means 13. A monostable flip-flop 22 feeds back the signal of the flip-flop 19 in order to make it impossible for two consecutive QRS complexes to trigger the delay means if switch 18 has been depressed for too long a period of time.

Switch means 13 comprises a relay, which in response to a signal from a delay member 11 will discharge a flash-aggregate which is provided for an optical pumping of the laser 3. The discharge lasts approximately 800 μs. During this time, two laser pulses are obtained through control or operation of the Pockles cells of the laser. The time between the laser pulses can thus be adjusted between 0 and 800 μs. The switch means 13 as well as the remainder of the laser 3 is commercially available for example the unit may be a "holobeam 651", which is sold by Holobeam Laser, Inc., of New Jersey.

Due to the two flashes of the laser 3, two separate holograms will be recorded on the film and a pattern of interference fringes will result after the film has been developed and exposed to a beam of coherent light. An example of the pattern of interference fringes is illustrated in FIG. 2. In FIG. 2, the neck region of the patient and the cardiac region are clearly recognizable on the exterior chest wall. Spacing or spatial intervals between interference fringes is a quantitive measurement of the movement of the body surface. The movement of the wall and the neck due to the pulsation of the carotid artery and the movement of the chest wall in the region of the heart can be clearly recognized. Accordingly, an image surface as this affords at a glance interpretation or evaluation of the movement of the body surface brought about by the activity of the heart during the time interval between the two hologram exposures. The time delay of the delay means 11 can be adjusted so that the optimum reproduction of the movements are recorded.

Thus, the significant feature of the invention is that the signal for the switching on of the laser 3 is derived from the patient by means of a transmitter which detects cardiac activity.

Although various minor modifications might be suggested by those versed in the art, it should be understood that we wish to embody within the scope of the patent granted hereon all such modifications as reasonably and properly come within the scope of our contribution to the art.

We claim:

1. In a holographic system for recording movements of a body surface of a patient, said system including a source of coherent light for projecting light on a body surface to create an object wave and having means for creating a reference wave, a film carrier for photographic film disposed to simultaneously record the object and reference waves to form a hologram thereof, and switch means for double pulse switching of said source at predetermined intervals so that two separate holograms of the body surface are recorded with each hologram being at a different time interval of the movement of the body surface, the improvements comprising transmitter means for sensing cardiac activity of the patient and creating a signal to activate said switch means, said transmitter means including means for determining an EKG of the patient and signal processing means for activating said switch means at a predetermined interval of an EKG cycle, said signal processing means being connected to said means for determining an EKG.

2. In a holographic system according to claim 1, wherein the signal processing means includes a detector means and a delay means, said detector means creating a switching on pulse during a predetermined portion of an EKG cycle and applying the pulse to the delay means and the switch means, said delay means delaying the pulse and then applying it to the switch means so that operation of the switch means can be delayed for a given time after detection of the portion of the EKG cycle.

* * * * *